US007892776B2

(12) United States Patent
Taylor et al.

(10) Patent No.: US 7,892,776 B2
(45) Date of Patent: Feb. 22, 2011

(54) SCREENING ASSAY TO IDENTIFY MODULATORS OF PROTEIN KINASE A

(75) Inventors: Susan S. Taylor, Del Mar, CA (US); Sanjay A. Saldanha, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 233 days.

(21) Appl. No.: 12/151,318

(22) Filed: May 5, 2008

(65) Prior Publication Data

US 2009/0061442 A1 Mar. 5, 2009

Related U.S. Application Data

(60) Provisional application No. 60/927,799, filed on May 4, 2007.

(51) Int. Cl.
C12Q 1/46 (2006.01)
(52) U.S. Cl. .............................. 435/15; 435/6; 536/23.2
(58) Field of Classification Search .................. 435/15, 435/6, 69.1; 536/23.2
See application file for complete search history.

(56) References Cited

U.S. PATENT DOCUMENTS

| | | |
|---|---|---|
| 3,536,809 A | 10/1970 | Appelzweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,197,350 B1 | 3/2001 | Yamagata et al. |
| 6,239,865 B1 | 5/2001 | Paritsky et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 6,740,634 B1 | 5/2004 | Saikawa et al. |
| 2008/0248008 A1* | 10/2008 | Carlson et al. ............ 424/93.21 |

OTHER PUBLICATIONS

Saldanha S. et al. Assay Principle for Modulators of Protein-Protein Interactions . . . Analytical Chem 78(24)8265-72, Dec. 15, 2006.*
Akamine, P., Madhusudan, Brunton, L.L., Ou, H.D., Canaves, J.M., Xuong, N.H., and Taylor, S.S. (2004). Balanol analogues probe specificity determinants and the conformational malleability of the cyclic 3',5'-adenosine monophosphate-dependent protein kinase catalytic subunit. Biochemistry 43, 85-96.
Beasley, J.R., McCoy, P.M., Walker, T.L., and Dunn, D.A. (2004). Miniaturized, ultra-high throughput screening of tyrosine kinases using homogeneous, competitive fluorescence immunoassays. Assay Drug Dev Technol 2, 141-151.
Casey, M., Vaughan, C.J., He, J., Hatcher, C.J., Winter, J.M., Weremowicz, S., Montgomery, K., Kucherlapati, R., Morton, C.C., and Basson, C.T. (2000). Mutations in the protein kinase A R1alpha regulatory subunit cause familial cardiac myxomas and Carney complex. J Clin Invest 106, R31-38.
Cheng, H.C., Kemp, B.E., Pearson, R.B., Smith, A.J., Misconi, L., Van Patten, S.M., and Walsh, D.A. (1986). A potent synthetic peptide inhibitor of the cAMP-dependent protein kinase. J Biol Chem 261, 989-992.

(Continued)

*Primary Examiner*—Ralph Gitomer
(74) *Attorney, Agent, or Firm*—Kilpatrick Townsend & Stockton LLP

(57) ABSTRACT

Methods for screening compounds for their activity as a protein kinase A modulators are provided. The methods are based on fluorescence polarization of peptide probes to identify drug candidates that act by activating or inhibiting the catalytic function of PKA. In certain embodiments, the methods are adapted for high throughput screening.

25 Claims, 12 Drawing Sheets

OTHER PUBLICATIONS

Chijiwa, T., Mishima, A., Hagiwara, M., Sano, M., Hayashi, K., Inoue, T., Naito, K., Toshioka, T., and Hidaka, H. (1990). Inhibition of forskolin-induced neurite outgrowth and protein phosphorylation by a newly synthesized selective inhibitor of cyclic AMP-dependent protein kinase, N-[2-(p-bromocinnamylamino)ethyl]-5-isoquinolinesulfonamide (H-89), of PC12D pheochromocytoma cells. J Biol Chem 265, 5267-5272.

Feliciello, A., Gottesman, M.E., and Avvedimento, E.V. (2001). The biological functions of A-kinase anchor proteins. J Mol Biol 308, 99-114.

Gangal, M., Cox, S., Lew, J., Clifford, T., Garrod, S.M., Aschbaher, M., Taylor, S.S., and Johnson, D.A. (1998). Backbone flexibility of five sites on the catalytic subunit of cAMP-dependent protein kinase in the open and closed conformations. Biochemistry 37, 13728-13735.

Gesellchen, F., Prinz, A., Zimmermann, B., and Herberg, F.W. (2006). Quantification of cAMP antagonist action in vitro and in living cells. Eur J Cell Biol.

Glass, D.B., Cheng, H.C., Mende-Mueller, L., Reed, J., and Walsh, D.A. (1989). Primary structural determinants essential for potent inhibition of cAMP-dependent protein kinase by inhibitory peptides corresponding to the active portion of the heat-stable inhibitor protein. J Biol Chem 264, 8802-8810.

Herberg, F.W., Dostmann, W.R., Zorn, M., Davis, S.J., and Taylor, S.S. (1994). Crosstalk between domains in the regulatory subunit of cAMP-dependent protein kinase: influence of amino terminus on cAMP binding and holoenzyme formation. Biochemistry 33, 7485-7494.

Huang, X. (2003). Fluorescence polarization competition assay: the range of resolvable inhibitor potency is limited by the affinity of the fluorescent ligand. J Biomol Screen 8, 34-38.

Kim, C., Xuong, N.H., and Taylor, S.S. (2005). Crystal structure of a complex between the catalytic and regulatory (RIalpha) subunits of PKA. Science 307, 690-696.

Kirschner, L.S., Carney, J.A., Pack, S.D., Taymans, S.E., Giatzakis, C., Cho, Y.S., Cho-Chung, Y.S., and Stratakis, C.A. (2000). Mutations of the gene encoding the protein kinase A type I-alpha regulatory subunit in patients with the Carney complex. Nat Genet 26, 89-92.

Krishna and Shekar; (2005). Cytochrome P450 3A: Genetic Polymorphisms and Interethnic Differences. Methods Find Exp Clin Pharmacol 27(8): 559-567.

Lania, A.G., Mantovani, G., Ferrero, S., Pellegrini, C., Bondioni, S., Peverelli, E., Braidotti, P., Locatelli, M., Zavanone, M.L., Ferrante, E., Bosari, S., Beck-Peccoz, P., and Spada, A. (2004). Proliferation of transformed somatotroph cells related to low or absent expression of protein kinase a regulatory subunit 1A protein. Cancer Res 64, 9193-9198.

Lew, J., Coruh, N., Tsigelny, I., Garrod, S., and Taylor, S.S. (1997). Synergistic binding of nucleotides and inhibitors to cAMP-dependent protein kinase examined by acrylodan fluorescence spectroscopy. J Biol Chem 272, 1507-1513.

Mallari, R., Swearingen, E., Liu, W., Ow, A., Young, S.W., and Huang, S.G. (2003). A generic high-throughput screening assay for kinases: protein kinase a as an example. J Biomol Screen 8, 198-204.

Miick, S.M., Jalali, S., Dwyer, B.P., Havens, J., Thomas, D., Jimenez, M.A., Simpson, M.T., Zile, B., Huss, K.L., and Campbell, R.M. (2005). Development of a microplate-based, electrophoretic fluorescent protein kinase a assay: comparison with filter-binding and fluorescence polarization assay formats. J Biomol Screen 10, 329-338.

Miller, W.R. (2002). Regulatory subunits of PKA and breast cancer. Ann N Y Acad Sci 968, 37-48.

Nesterova, M.V., and Cho-Chung, Y.S. (2004). Antisense protein kinase A RIalpha inhibits 7,12-dimethylbenz(a)anthracene-induction of mammary cancer: blockade at the initial phase of carcinogenesis. Clin Cancer Res 10, 4568-4577.

Nikolovska-Coleska, Z., Wang, R., Fang, X., Pan, H., Tomita, Y., Li, P., Roller, P.P., Krajewski, K., Saito, N.G., Stuckey, J.A., and Wang, S. (2004). Development and optimization of a binding assay for the XIAP BIR3 domain using fluorescence polarization. Anal Biochem 332, 261-273.

Owicki, J.C. (2000). Fluorescence polarization and anisotropy in high throughput screening: perspectives and primer. J Biomol Screen 5, 297-306.

Parker, G.J., Law, T.L., Lenoch, F.J., and Bolger, R.E. (2000). Development of high throughput screening assays using fluorescence polarization: nuclear receptor-ligand-binding and kinase/phosphatase assays. J Biomol Screen 5, 77-88.

Pin SS Analysis of protein-peptide interaction by a miniaturized fluorescence polarization assay using cyclin-dependent kinase 2/cyclin E as a model system. Anal Biochem. Nov. 15, 1999;275(2):156-61.

Saldanha SA Assay principle for modulators of protein-protein interactions and its application to non-ATP-competitive ligands targeting protein kinase A. Anal Chem. Dec. 15, 2006;78(24):8265-72.

Schneider, T.L., Mathew, R.S., Rice, K.P., Tamaki, K., Wood, J.L., and Schepartz, A. (2005). Increasing the kinase specificity of k252a by protein surface recognition. Org Lett 7, 1695-1698.

Schwede, F., Maronde, E., Genieser, H., and Jastorff, B. (2000). Cyclic nucleotide analogs as biochemical tools and prospective drugs. Pharmacol Ther 87, 199-226.

Seethala, R., and Menzel, R. (1998). A fluorescence polarization competition immunoassay for tyrosine kinases. Anal Biochem 255, 257-262.

Shabb, J.B., Ng, L., and Corbin, J.D. (1990). One amino acid change produces a high affinity cGMP-binding site in cAMP-dependent protein kinase. J Biol Chem 265, 16031-16034.

Singh, P., Lillywhite, B., Bannaghan, C., and Broad, P. (2005). Using IMAP technology to identify kinase inhibitors: comparison with a substrate depletion approach and analysis of the nature of false positives. Comb Chem High Throughput Screen 8, 319-325.

Skalhegg, B.S., and Tasken, K. (2000). Specificity in the cAMP/PKA signaling pathway. Differential expression,regulation, and subcellular localization of subunits of PKA. Front Biosci 5, D678-693.

Skalhegg, B.S., Funderud, A., Henanger, H.H., Hafte, T.T., Larsen, A.C., Kvissel, A.K., Eikvar, S., and Orstavik, S. (2005). Protein kinase A (PKA)—a potential target for therapeutic intervention of dysfunctional immune cells. Curr Drug Targets 6, 655-664.

Son, Y.K., Park, W.S., Kim, S.J., Earm, Y.E., Kim, N., Youm, J.B., Warda, M., Kim, E., and Han, J. (2006). Direct inhibition of a PKA inhibitor, H-89 on KV channels in rabbit coronary arterial smooth muscle cells.

Biochem Biophys Res Commun 341, 931-937.

Sportsman, J.R., Gaudet, E.A., and Boge, A. (2004). Immobilized metal ion affinity-based fluorescence polarization (IMAP): advances in kinase screening. Assay Drug Dev Technol 2, 205-214.

Su, Y., Dostmann, W.R., Herberg, F.W., Durick, K., Xuong, N.H., Ten Eyck, L., Taylor, S.S., and Varughese, K.I. (1995). Regulatory subunit of protein kinase A: structure of deletion mutant with cAMP binding domains. Science 269, 807-813.

Taimi, M., Breitman, T.R., and Takahashi, N. (2001). Cyclic AMP-dependent protein kinase isoenzymes in human myeloid leukemia (HL60) and breast tumor (MCF-7) cells. Arch Biochem Biophys 392, 137-144.

Vedvik, K.L., Eliason, H.C., Hoffman, R.L., Gibson, J.R., Kupcho, K.R., Somberg, R.L., and Vogel, K.W. (2004). Overcoming compound interference in fluorescence polarization-based kinase assays using far-red tracers. Assay Drug Dev Technol 2, 193-203.

Von Leoprechting, A., Kumpf, R., Menzel, S., Reulle, D., Griebel, R., Valler, M.J., and Buttner, F.H. (2004). Miniaturization and validation of a high-throughput serine kinase assay using the AlphaScreen platform. J Biomol Screen 9, 719-725.

Wu, J., Brown, S., Xuong, N.H., and Taylor, S.S. (2004). RIalpha subunit of PKA: a cAMP-free structure reveals a hydrophobic capping mechanism for docking cAMP into site B. Structure 12, 1057-1065.

Wu, J., Jones, J.M., Nguyen-Huu, X., Ten Eyck, L.F., and Taylor, S.S. (2004). Crystal structures of RIalpha subunit of cyclic adenosine 5'-monophosphate (cAMP)-dependent protein kinase complexed with (Rp)-adenosine 3',5'-cyclic monophosphothioate and (Sp)-adenosine 3',5'-cyclic monophosphothioate, the phosphothioate analogues of cAMP. Biochemistry 43, 6620-6629.

Xia, W., Rininsland, F., Wittenburg, S.K., Shi, X., Achyuthan, K.E., McBranch, D.W., and Whitten, D.G. (2004). Applications of fluorescent polymer superquenching to high throughput screening assays for protein kinases. Assay Drug Dev Technol 2, 183-192.

Zhang, J.H., Chung, T.D., and Oldenburg, K.R. (1999). A Simple Statistical Parameter for Use in Evaluation and Validation of High Throughput Screening Assays. J Biomol Screen 4, 67-73.

Zhang, L., and Insel, P.A. (2004). The pro-apoptotic protein Bim is a convergence point for cAMP/protein kinase A- and glucocorticoid-promoted apoptosis of lymphoid cells. J Biol Chem 279, 20858-20865.

Zhang, R., Mayhood, T., Lipari, P., Wang, Y., Durkin, J., Syto, R., Gesell, J., McNemar, C., and Windsor, W. (2004). Fluorescence polarization assay and inhibitor design for MDM2/p53 interaction. Anal Biochem 331, 138-146.

* cited by examiner

SEQUENCE LISTING

<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: peptide probe

<400> SEQUENCE: 1

Thr Thr Tyr Ala Asp Phe Ile Ala Ser Gly Arg Thr Gly Arg Arg Asn
1               5                   10                  15

Ala Ile His Asp
            20

<210> SEQ ID NO 2
<211> LENGTH: 7
<212> TYPE: PRT
<213> ORGANISM: Artificial Sequence
<220> FEATURE:
<223> OTHER INFORMATION: peptide substrate

<400> SEQUENCE: 2

Leu Arg Arg Ala Ser Leu Gly
1               5

SCREENING ASSAY TO IDENTIFY MODULATORS OF PROTEIN KINASE A

RELATED APPLICATIONS

This application claims priority to U.S. Provisional Patent Application No. 60/927,799, filed May 4, 2007, entitled "A High Throughput Assay to Identify non-ATP-Competitors Targeting Protein Kinase A." The disclosure of the above-referenced application is incorporated by reference herein in its entirety.

FIELD

Provided herein is a method for screening compounds that act as modulators of the biological activity of protein kinase A. The method is based on fluorescence polarization (FP) to identify drug candidates that act by specifically targeting Protein Kinase A (PKA). The drug candidate compounds mediate their effect by activating or inhibiting the catalytic function of PKA. Also provided are compounds identified by the screening method. The compounds identified using the method are used in pharmacological compositions and methods for the treatment of various diseases in which PKA activity is implicated.

BACKGROUND

Protein kinase A (PKA) is a ubiquitous serine/threonine protein kinase involved in cell signaling by phosphorylating intracellular protein substrates in response to the secondary messenger, cyclic adenosine monophosphate (cAMP). The PKA holoenzyme is composed of two catalytic (C-) and two regulatory (R-) subunits that form an inactive tetramer. Upon the binding of cAMP to the R-subunits (each having two cAMP-binding sites), the tetramer dissociates into a dimer of R-subunits and two catalytically active C-subunits, thus enabling the phosphorylation of downstream PKA substrates.

The R-subunit has two major roles. First, it prevents access to the substrate-binding site on the C-subunit (in the absence of cAMP), and second, it determines subcellular localization of this kinase via specific interactions with A-kinase anchoring proteins (AKAPs). There are four isoforms of the PKA regulatory subunit (RIα, RIβ, RIIα, and RIIβ) that differ in their abundance, affinity for the PKA catalytic subunit, sensitivity to cAMP, and specificity for different AKAPs. This diversity determines cell-specific PKA localization and diversifies PKA-mediated signaling [Feliciello, A., et al., (2001), The biological functions of A-kinase anchor proteins, J Mol Biol 308, 99-114., Skalhegg, B. S., and Tasken, K. (2000), Specificity in the cAMP/PKA signaling pathway. Differential expression, regulation, and subcellular localization of subunits of PKA. Front Biosci 5, D678-693].

PKA is implicated in several cancers including endocrine (e.g. carney complex [Casey, M., et al., (2000), Mutations in the protein kinase A R1alpha regulatory subunit cause familial cardiac myxomas and Carney complex. J Clin Invest 106, R31-38., Kirschner, L. S. et al., (2000), Mutations of the gene encoding the protein kinase A type I-alpha regulatory subunit in patients with the Carney complex. Nat Genet. 26, 89-92] and pituitary [Lania, A. G., et al., (2004), Proliferation of transformed somatotroph cells related to low or absent expression of protein kinase a regulatory subunit 1A protein, Cancer Res 64, 9193-9198]) and non-endocrine (e.g. breast [Taimi, M., et al., (2001), Cyclic AMP-dependent protein kinase isoenzymes in human myeloid leukemia (HL60) and breast tumor (MCF-7) cells, Arch Biochem Biophys 392, 137-144., Miller, W. R. (2002), Regulatory subunits of PKA and breast cancer, Ann N Y Acad Sci 968, 37-48]). Additionally, PKA is suggested to be a therapeutic target for diseases of the immune system (e.g. SLE and HIV) [Skalhegg, et al., (2005), Protein kinase A (PKA)—a potential target for therapeutic intervention of dysfunctional immune cells, Curr Drug Targets 6, 655-664]. However, given the ubiquitous nature of this protein kinase, targeting the ATP-binding site of the catalytic subunit, would likely kill healthy cells.

Recently, an alternative strategy was used to target PKA in disease. Several studies have shown that disease progression in some cancers is correlated with abnormally high levels of the RIα isoform [Taimi, M., et al., (2001), Cyclic AMP-dependent protein kinase isoenzymes in human myeloid leukemia (HL60) and breast tumor (MCF-7) cells. Arch Biochem Biophys 392, 137-144., Miller, W. R. (2002). Regulatory subunits of PKA and breast cancer. Ann N Y Acad Sci 968, 37-48], and it is presumably the abundance of type Iα PKA holoenzyme (PKA-Iα) that causes aberrant phosphorylation and cancer. As a result, RIα antisense therapy is currently undergoing phase I/II clinical trials for the treatment of patients with malignant solid tumors [Nesterova, M. V., and Cho-Chung, Y. S., (2004), Antisense protein kinase A RIαalpha inhibits 7,12-dimethylbenz(a)anthracene-induction of mammary cancer: blockade at the initial phase of carcinogenesis, Clin Cancer Res 10, 4568-4577]. A small molecule that selectively inhibits the catalytic function of PKA-Iα holoenzyme would mimic the effect of RIα antisense therapy by repressing aberrant phosphorylation. In addition, a PKA-Iα antagonist has been suggested as a therapeutic agent to improve T cell responsiveness to HIV [Skalhegg, B. S., et al., (2005), Protein kinase A (PKA)—a potential target for therapeutic intervention of dysfunctional immune cells, Curr Drug Targets 6, 655-664]. On the other hand, a small molecule that selectively activates PKA may also be of benefit. For example, S49 T-lymphoma cells have been reported to undergo cAMP stimulated apoptosis through activation of PKA [Zhang, L., and Insel, P. A., (2004), The pro-apoptotic protein Bim is a convergence point for cAMP/protein kinase A- and glucocorticoid-promoted apoptosis of lymphoid cells, J Biol Chem 279, 20858-20865].

PKA Small Molecule Ligands

Two classes of small molecule effectors targeting PKA have been described. The first are ATP competitive that inhibit the catalytic function via interaction with the ATP-binding site of the C-subunit. However, ATP-competitors, such as H89 [Chijiwa, T., et al., (1990), Inhibition of forskolin-induced neurite outgrowth and protein phosphorylation by a newly synthesized selective inhibitor of cyclic AMP-dependent protein kinase, N-[2-(p-bromocinnamylamino)ethyl]-5-isoquinolinesulfonamide (H-89), of PC 12D pheochromocytoma cells. J Biol Chem 265, 5267-5272] and balanol [Akamine, P., et al., (2004), Balanol analogues probe specificity determinants and the conformational malleability of the cyclic 3',5'-adenosine monophosphate-dependent protein kinase catalytic subunit, Biochemistry 43, 85-96] inhibit other protein kinases and non-related cellular receptors [Son, Y. K., et al., (2006), Direct inhibition of a PKA inhibitor, H-89 on KV channels in rabbit coronary arterial smooth muscle cells, Biochem Biophys Res Commun 341, 931-937].

The second class comprises cAMP competitors [Schwede, F., et al., (2000), Cyclic nucleotide analogs as biochemical tools and prospective drugs. Pharmacol Ther 87, 199-226]. Activation of the holoenzyme is induced by binding of four cAMP molecules, two per R-subunit. Cell permeable derivatives of cAMP act as agonists (activating the holoenzyme in the same way as cAMP itself) or antagonists (competing with cAMP for binding to the R-subunits but not activating the holoenzyme). However, the major drawback with this class of small molecules are their poor affinity for the PKA regulatory subunits (micromolar) leading to poor cellular responses.

Targeting the cAMP Binding Sites

The cAMP binding sites are targets for novel non-ATP competitive effectors of PKA function. To date, only cyclic nucleotide analogs have been reported to bind to these sites. However, as the cyclic phosphate group is a strict requirement for binding, these compounds exhibit poor in-vivo efficacy. Crystal structures for the free R-subunits [Wu, J., Brown, et al., (2004), RIα subunit of PKA: a cAMP-free structure reveals a hydrophobic capping mechanism for docking cAMP into site B. *Structure* 12, 1057-1065] as well as R-subunit bound to cAMP analogs [Wu, J., et al., (2004), Crystal structures of RIalpha subunit of cyclic adenosine 5'-monophosphate (cAMP)-dependent protein kinase complexed with (Rp)-adenosine 3',5'-cyclic monophosphothioate and (Sp)-adenosine 3',5'-cyclic monophosphothioate, the phosphothioate analogues of cAMP, *Biochemistry* 43, 6620-6629] and most recently R-subunit bound to the C-subunit [Kim, C., et al., (2005), Crystal structure of a complex between the catalytic and regulatory (RIα) subunits of PKA, *Science* 307, 690-696] allow correlation between sequence and structure. The R-subunit is composed of two homologous domains with one cAMP binding site each (named A and B sites) residing in each domain. Although both A and B sites bind cAMP with high affinity, their structural and sequence (FIG. 1) divergence suggests that small molecules can be discovered that distinguish between them. Indeed, synthetic cAMP analogs have been designed that bind preferentially to one site [Schwede, F., et al., (2000), Cyclic nucleotide analogs as biochemical tools and prospective drugs, *Pharmacol Ther* 87, 199-226].

There is also sufficient sequence divergence between RI and RII isoforms to suggest that selective binders may be designed. Inspection of the residues directly in contact with cAMP (FIG. 1) shows that 6 out of 19 residues in the A site and 11 out of 22 residues in the B site differ between types I and II. The discovery of isoform specific R-binders then opens up the possibility for targeting only the disease associated forms of PKA.

Therefore, there is a need for an assay system, amenable to high throughput screening, to detect small molecule agonists or antagonists for the Iα PKA holoenzyme.

SUMMARY

Provided herein is a fluorescent polarization (FP) based method for screening compounds for their ability to modulate an activity of protein kinase A. The screening method encompasses the steps of i) contacting a test compound with a mixture comprising a fluorescently-labeled peptide probe, a cyclic nucleotide or an analog thereof, a C-subunit and an R-subunit of protein kinase A; and ii) comparing the fluorescent polarization of the mixture before and after contacting the test compound. The method provided herein can be used with any of the four regulatory isoforms of R-subunit. In certain embodiments, the methods are adapted for high throughput screening.

The methods can be used to screen agonists and antagonists of PKA holoenzyme. Agonists are compounds that weaken the R-C complex allowing the fluorescently-labeled peptide probe to compete for binding to C-subunit, facilitating an increase of the bound probe fraction and as a consequence, increasing its FP value. In contrast, an antagonist is a compound that shields the R-C complex by preventing the cyclic nucleotide or analog thereof from binding to the R-subunit. Consequently, less C-subunit will be available to bind to fluorescently-labeled peptide probe and the fraction of bound probe will be reduced resulting decreased FP signal.

In some embodiments, the compounds are agonists (PKA activators that stimulate holoenzyme dissociation) or antagonists (competitive or non-competitive inhibitors of cAMP-induced dissociation) of type Iα PKA holoenzyme. In some embodiments, the compounds that can be detected by the screening method provided herein specifically interact with the regulatory RIα subunit, but not the catalytic subunit. In one embodiment, the compounds bind to binding sites (i.e. non-ATP binding sites) in the catalytic subunit and act as antagonists or agonists.

The screening method utilizes a fluorescently-labeled peptide probe that acts as an inhibitor of protein kinase A. In one embodiment, the peptide probe is selected from heat stable protein kinase inhibitors (PKIs). PKIs are a family of small proteins that inhibit PKA by binding to the substrate-binding site of the catalytic subunit. In certain embodiments, the peptide probe binds to the catalytic subunit with sub-nanomolar affinity. The high affinity binding motif is found at residues 5 to 24 of PKI, and the respective 20-mer peptide spanning this range (named PKI (5-24) or IP20) binds with Kd of 2.3 nM [Glass, D. B., et al., (1989), Primary structural determinants essential for potent inhibition of cAMP-dependent protein kinase by inhibitory peptides corresponding to the active portion of the heat-stable inhibitor protein, *J Biol Chem* 264, 8802-8810].

In the screening method provided herein, the peptide probe, such as IP20, and the R-subunit bind to overlapping sites on the C-subunit and are competitors. The binding of C-subunit to fluorescently labeled IP20 acts as a probe for the interaction of the C- and R-subunits with fluorescence polarization (FP) as readout. Scheme 1 summarizes the principle behind this assay with c-AMP as an exemplary cyclic nucleotide and IP20 as an exemplary peptide probe. In the absence of the c-AMP, the RIα subunit affinity for the catalytic subunit (apparent Kd of 0.39 nM [Herberg, F. W., et al., (1994), Crosstalk between domains in the regulatory subunit of cAMP-dependent protein kinase: influence of amino terminus on cAMP binding and holoenzyme formation, *Biochemistry* 33, 7485-7494]) is an order of magnitude higher than that of IP20 (apparent Kd of 2.3 nM). However, in the presence of the cyclic nucleotide the R-C complex is weakened allowing IP20 to compete for binding to C-subunit.

Further provided herein are compounds capable of modulating the activity of protein kinase A identified by the screening method provided herein.

In some embodiments, provided herein are methods of using such identified compounds in pharmaceutical compositions for the treatment, prevention and amelioration of various PKA-mediated conditions, including, but not limited to several cancers and diseases of the immune system.

DETAILED DESCRIPTION

A. Definitions

Figure 1:
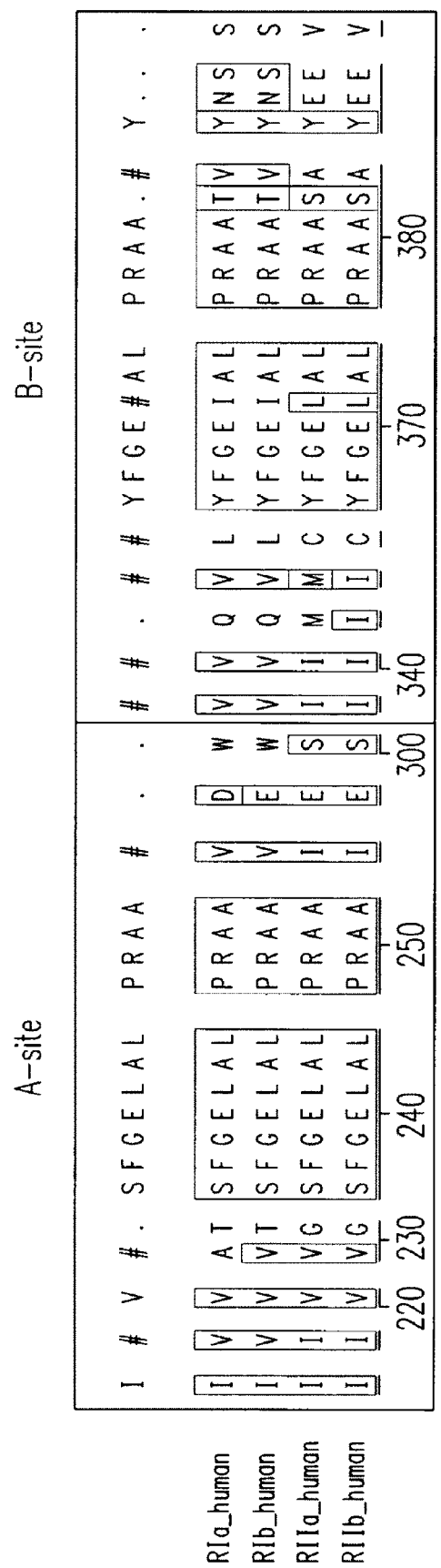
FIG. 1 depicts comparison of RI and RII residues in the A and B sites that directly contact cAMP. Alignment showing the sites involved in cAMP binding.
Figure 2A:
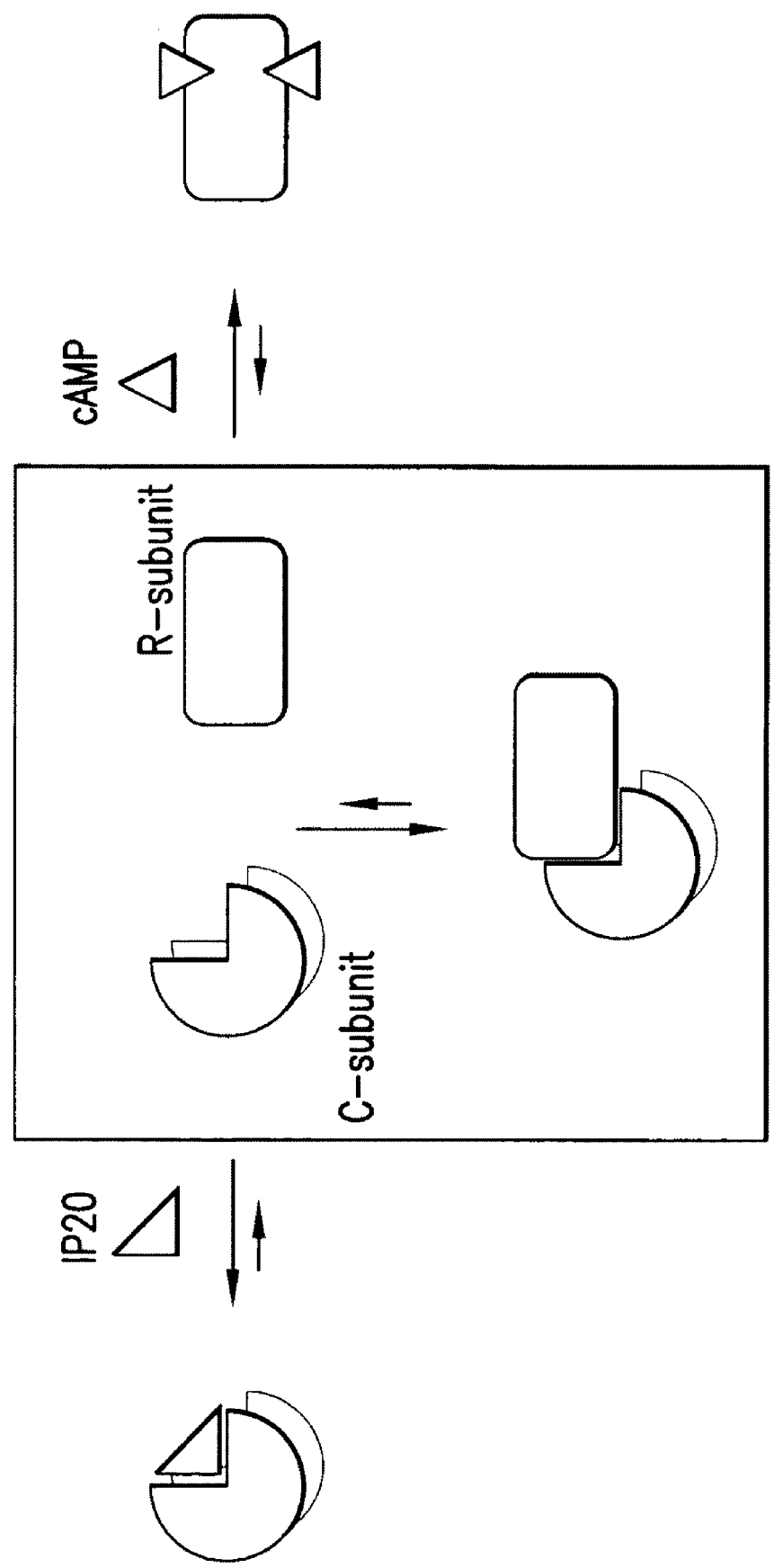
FIG. 2A demonstrates the principle behind the screening method provided herein. In the absence of cAMP, the RIα subunit affinity for the catalytic subunit is higher than that of IP20. However, in the presence of a cyclic nucleotide the R-C complex is weakened allowing IP20 to compete for binding to C-subunit.
Figure 2B:
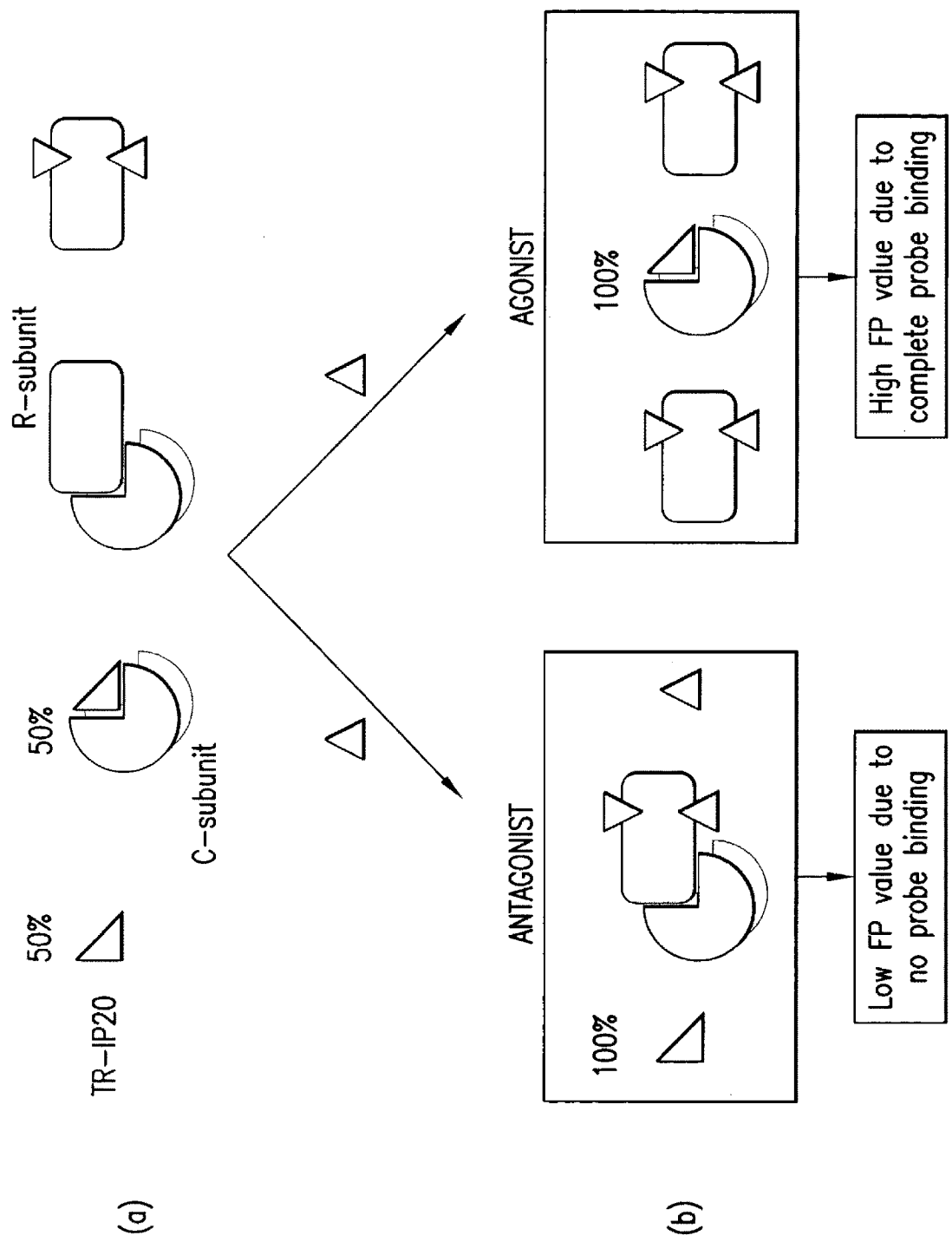
FIG. 2B demonstrates the principle in the high throughput (HTS) format: (a) an agonist at its $EC_{50}$ concentration will allow 50% of TR-IP20 to bind, eliciting a half maximal FP response. (b) Another agonist (green triangle) will further weaken the R-C complex allowing more TR-IP20 to bind and increasing the FP signal. An antagonist will compete with the agonist and shield the R-C complex, preventing binding of TR-IP20 to C-subunit and decreasing the FP signal.

Unless defined otherwise, all technical and scientific terms used herein have the same meaning as is commonly understood by one of ordinary skill in the art to which the claimed subject matter belongs. All patents, applications, published applications and other publications are incorporated by reference in their entirety. In the event that there are a plurality of definitions for a term herein, those in this section prevail unless stated otherwise.

Protein kinase A is the protein kinase that serves as the major intracellular receptor for cyclic AMP (cAMP). As used herein the term "Protein kinase A" or "PKA" refers to the ubiquitous serine/threonine protein kinase involved in cell signaling by phosphorylating intracellular protein substrates in response to the secondary messenger, cyclic adenosine monophosphate (cAMP). It is also intended to encompass the array of PKA isozymes identified in various organisms and any natural or synthetic substance that may act to exert a physiological response exerted by PKA or bind to molecules normally bound by the natural PKA.

The PKA is a tetrameric holoenzyme complex composed of separate regulatory and catalytic subunits. In mammalian cells, the catalytic subunit isoforms include Cα, Cβ, and Cγ. The regulatory subunit classes are R1 (RI) and R2 (RII), with two isoforms of each class (i.e., R1A, R1B, R2A, and R2B).

The "C subunit" as used herein refers to the catalytic subunit of protein kinase A and encompasses any natural or synthetic substance that may act to exert a physiological response exerted by the catalytic subunit of PKA or bind to molecules normally bound by the natural catalytic subunit of PKA.

The "R subunit" as used herein refers to the regulatory subunit of protein kinase A and encompasses any natural or synthetic substance that may act to exert a physiological response exerted by the regulatory subunit of PKA or bind to molecules normally bound by the natural regulatory subunit of PKA.

As used herein, "substrate" or "peptide probe" is a molecule which is subject to phosphorylation by protein kinase A. The substrate contains at least one residue that can be phosphorylated by protein kinase A. The substrates for protein kinase A include, but are not limited to, natural and non-natural peptides and their analogs, that can be phosphorylated by protein kinase A.

As used herein, "peptide" encompasses any peptide comprised of amino acids, amino acid analogs, peptidomimetics or combinations thereof. The term "amino acids" refers either to natural and/or unnatural synthetic amino acids, including both the D and L isomers, and encompasses any amine containing acid compound.

As used herein "cyclic nucleotide" refers to any nucleotide in which the phosphate group is bonded to two of the sugar's hydroxyl groups, forming a cyclical or ring structure. These include cyclic AMP and cyclic GMP, which function as secondary messengers associated with PKA.

The term "agonist," as used herein, refers to a molecule which, when bound to protein kinase A or at least one subunit of the holoenzyme, causes a change which increases the activity of the kinase or the subunit. Agonists may include any molecules which bind or interact with protein kinase A or any of its subunits.

The terms "antagonist" or "inhibitor," as used herein, refer to a molecule which, when bound to protein kinase A or at least one subunit of the holoenzyme, blocks or reduces the activity of protein kinase A or any of its subunits. Antagonists and inhibitors may include any molecules which bind or interact with any portion of the protein kinase A holoenzyme (e.g., one or more of the subunits).

The term "modulate," as used herein, refers to a change or an alteration in the biological activity of protein kinase A or any of its subunits. Modulation may be an increase or a decrease in protein activity, a change in binding characteristics, or any other change in the biological, functional, or immunological properties of protein kinase A or any of its subunits.

As used herein, treatment means any manner in which one or more of the symptoms of a disease or disorder are ameliorated or otherwise beneficially altered.

The term "compound" or "test compound" refers to any chemical entity, pharmaceutical, drug, and the like that can be used to treat, ameliorate or prevent symptoms associated with a disease mediated by PKA activity. Compounds comprise both known and potential therapeutic compounds. A compound can be determined to be therapeutic by screening using the screening methods provided herein.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein "subject" is an animal, typically a mammal, including human, such as a patient.

As used herein, "sample" refers to cells (prokaryotic or eukaryotic), cell lysates or extracts of cell lysates (prokaryotic or eukaryotic, in any stage of purification), body fluids, tissue homogenates (or extracts in any stage of purification), and samples containing one or more purified or partially purified components. Thus, the methods encompass in vivo as well as in vitro assays, and include assays that are performed partially in vivo and partially in vitro.

The phrase "effective amount" as used herein means an amount required for prevention, treatment, or amelioration of one or more of the symptoms of diseases or disorders associated PKA.

B. Screening Methods

Provided herein is a fluorescent polarization based method for screening compounds for their ability to modulate an activity of protein kinase A. The screening method provided herein encompasses the steps of i) contacting a test compound with a mixture comprising a fluorescently-labeled peptide probe, a cyclic nucleotide or an analog thereof, a C-subunit and an R-subunit of protein kinase A; and ii) comparing the fluorescent polarization of the mixture before and after contacting the test compound.

In certain embodiments, the test compound is an agonist of PKA holoenzyme. Agonists are compounds that weaken the in-situ R-C complex formation allowing the fluorescently-labeled peptide probe to compete for binding to C-subunit, facilitating an increase of the bound probe fraction and as a consequence, increasing its FP value. In certain embodiments, the test compound is an antagonist of PKA holoenzyme. Antagonists are compounds that shield the R-C complex by preventing the cyclic nucleotide or analog thereof from binding to the R-subunit. Consequently, less C-subunit will be available to bind to fluorescently-labeled peptide probe and the fraction of bound probe will be reduced resulting decreased FP signal.

In one embodiment, the contacting step is carried out for a sufficient time to allow for the interaction between the C-subunit and the fluorescently labeled peptide probe to occur. Under the given screening conditions, the contact time can be empirically determined by one of skill in the art. In one embodiment, the peptide probe is selected from heat stable protein kinase inhibitors (PKIs). PKIs are a family of small proteins that inhibit PKA by binding to the substrate-binding site of the catalytic subunit. In certain embodiments, the peptide binds to the catalytic subunit with sub-nanomolar affinity. The high affinity binding motif is found at residues 5 to 24 of PKI. In one embodiment, the PKI for use herein is PKI (5-24) or IP20 [sequence: Thr-Thr-Tyr-Ala-Asp-Phe-Ile-Ala-Ser-Gly-Arg-Thr-Gly-Arg-Arg-Asn-Ala-Ile-His-Asp or SEQ ID 1] that binds to PKA with Kd of 2.3 nM. In some embodiments, the N-terminus of IP20 is labeled with carboxyfluorescein (Flu-IP20). In one embodiment, the concentration of Flu-IP20 is below the reported Kd for IP20. In another embodiment, the concentration of Flu-IP20 used is below 4.4 nM. In another embodiment, the concentration of Flu-IP20 used in the methods herein is about 4 nM, 3 nM, 2 nM, 1.8 nM, 1.5 nM, 1.3 nm or 1 nM. In another embodiment, the concentration of Flu-IP20 is about 1 nM.

Figure 5:
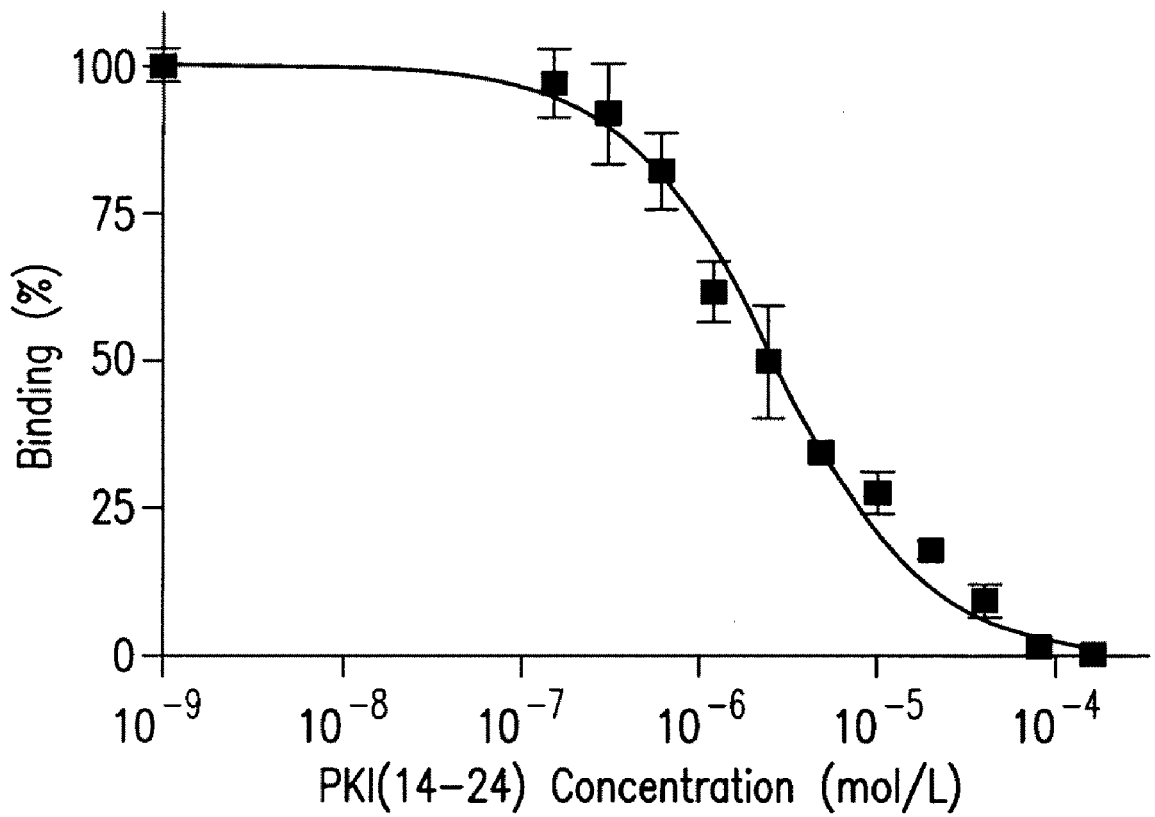
FIG. 5 shows binding by PKI (14-24) to C-subunit.

In one embodiment, IP20 is labeled at the N-terminus with a far-red dye, such as Texas red-X (TR-IP20). Other examples of far-red dyes include Cy5 and Phycoerythrins. In certain embodiments, the use of red-shifted fluorescent dyes in FP small molecule screening minimizes compound interference at longer excitation and emission wavelengths [Owicki, J. C. (2000), Fluorescence polarization and anisotropy in high throughput screening: perspectives and primer, *J Biomol Screen* 5, 297-306., Vedvik, K. L., et al., (2004), Overcoming compound interference in fluorescence polarization-based kinase assays using far-red tracers, *Assay Drug Dev Technol* 2, 193-203]. The binding characteristics of TR-IP20 with PKA are depicted in FIG. 5. In one embodiment, the concentration of TR-IP20 used in the methods herein is chosen to enable high precision FP readings and to reduce the effect of compound interference for small molecule screening.

In some embodiments, the use of TR-IP20 in the methods provided herein provides increases dynamic range for binding with the C-subunit (mP of bound peptide-mP of free peptide), from about 136 mP for Flu-IP20 to 237 mP for TR-IP20.

In one embodiment, the cyclic nucleotide for use herein is selected from cAMP, cGMP, cTzMP and deoxy-cAMP. In one embodiment, the cyclic nucleotide is cAMP. In one embodiment, the cyclic nucleotide is cGMP.

In one embodiment, the C subunit used is a wildtype or C199A mutant of the C-subunit. The C-subunit can be from any mammalian source. In one embodiment, the R-subunit used herein is a Δ1-91 deletion mutant of the type Iα R-subunit, lacking the dimerization docking domain and thus unable to dimerize. The corresponding deletion mutants in RIb, RIIa and RIIb can be used in the method provided herein to identify isoform specific PKA small molecule effectors. In certain embodiments, wildtype version of any of the four isoforms is used. The R-subunits can be from any mammalian source.

Compared to wildtype, the C199A mutant exhibits an identical binding profile with Flu-IP20, while the binding and activation characteristics of the Δ1-91 deletion mutant is almost the same as wildtype RIα [Herberg, F. W., et al., (1994), Crosstalk between domains in the regulatory subunit of cAMP-dependent protein kinase: influence of amino terminus on cAMP binding and holoenzyme formation. *Biochemistry* 33, 7485-7494]. The C199A mutant of recombinant murine catalytic subunit [Gangal, M., et al., (1998). Backbone flexibility of five sites on the catalytic subunit of cAMP-dependent protein kinase in the open and closed conformations. *Biochemistry* 37, 13728-13735] and the RIα (Δ1-91) deletion mutant [Su, Y., et al., (1995), Regulatory subunit of protein kinase A: structure of deletion mutant with cAMP binding domains, *Science* 269, 807-813] can be expressed and purified from *E. coli* as described elsewhere herein.

The concentration of C-subunit in the methods provided herein is chosen such that the interaction of the C-subunit with the desired concentration of fluorescent-labeled peptide probe results in a signal that is close to the saturation FP response. In some embodiments, the concentration of the C-subunit is less than about 75 nM. In some embodiments, the concentration of the C-subunit is about 50 nM-75 nM. In some embodiments, the concentration of the C-subunit is about 75 nM, 70 nM, 65 nM, 64 nM, 60 nM or 55 nM. In some embodiments, the concentration of the C-subunit is 64 nM.

In some embodiments, the concentration of R-subunit needed to form type Iα PKA holoenzyme, in-situ, is in about 1 to about 3 molar excess, or about 1.2 molar excess of the C-subunit.

In another embodiment, the concentration of Flu-IP20 is less than about 4.4 nM, the concentration of the C-subunit is less than about 75 nM and the concentration of R-subunit is in about 1 to about 3 molar excess of the C-subunit. In some embodiments, the concentration of Flu-IP20 is from about 1 nM-4 nM, the concentration of the C-subunit is about 50 nM-75 nM, and the concentration of R-subunit is in about 1 to about 3 molar excess of the C-subunit. In one embodiment, the following concentrations are used for screening: 1 nM of TR-IP20, 64 nM of C-subunit and 77 nM of R-subunit.

Figure 6:
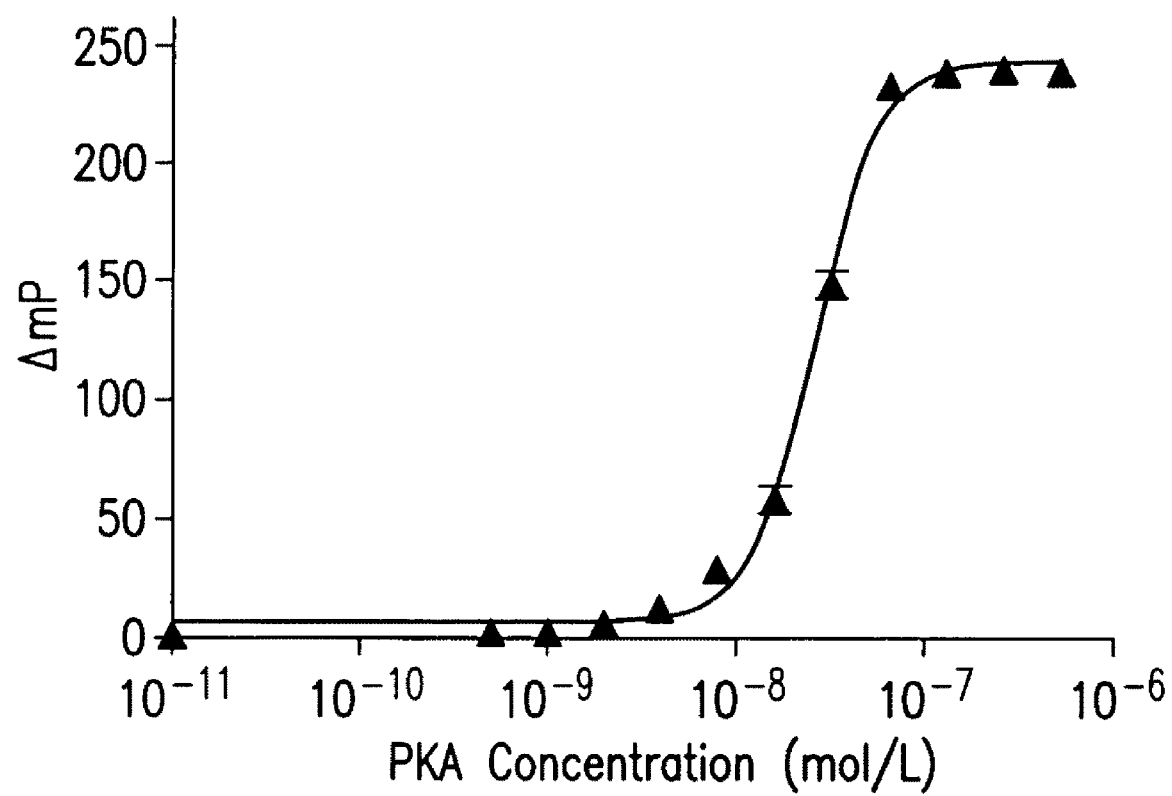
FIG. 6 illustrates dose response of 40 nM TR-IP20.
Figure 7:
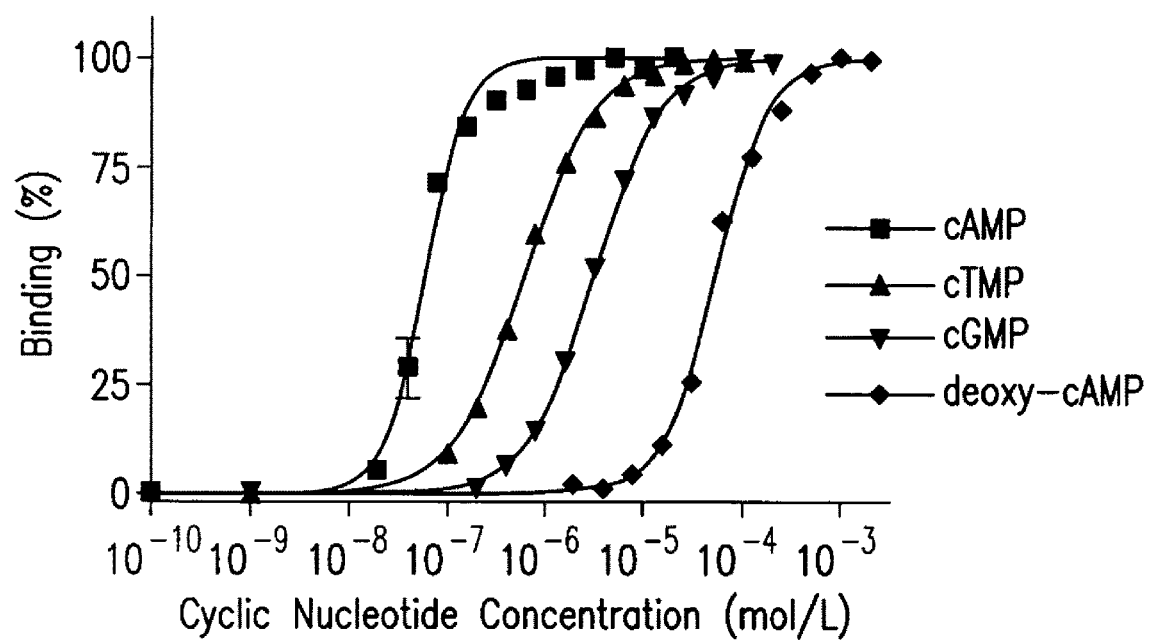
FIG. 7 illustrates binding of cAMP, cGMP, cTzMP and deoxy-cAMP to R-subunit.

The effectiveness of this system to probe R- and C-interactions can be gauged by measuring the change in FP signal at varying concentrations of four cyclic nucleotides (FIG. 6). The steep response for cAMP can be attributed to the high potency of cAMP coupled to a complex system where both TR-IP20 and RIα are used at concentrations well above their Kds. This rationale is inline with dose curves for the three other weaker cyclic nucleotides where the change in response is more gradual.

In one embodiment, a four-component system involving, TR-IP20, C-subunit, R-subunit and the cyclic nucleotide is adopted as a high throughput screening assay capable of detecting both agonists and antagonists of PKA holoenzyme (Scheme 2). In one embodiment, concentrations of C-subunit, R-subunit and the cyclic nucleotide are adjusted so that about half of fluorescently labeled IP20 is bound to the catalytic subunit and the other half is free. As a result, a half-maximal FP signal is observed that is proportional to the bound fraction of probe.

High Throughput Screening Assay

In certain embodiments, the screening method provided herein is adapted to high throughput screening (HTS). The most stable constructs for the C- and R-subunits are used to minimize reagent preparation for HTS. In one embodiment, the HTS method is automated and miniaturized, in particular it uses miniaturized wells and microfluidics controlled by a roboter. Several high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

In certain embodiments, the high throughput screening method comprises i) contacting a test compound with a mixture comprising a fluorescently-labeled peptide probe, a cyclic nucleotide or an analog thereof, a C-subunit and an R-subunit of protein kinase A; and ii) comparing the fluorescent polarization of the mixture before and after contacting the test compound.

In one embodiment, the concentrations of C-subunit, R-subunit and the cyclic nucleotide are adjusted so that about half of fluorescently labeled IP20 is bound to the catalytic subunit and the other half is free. As a result, a half-maximal FP signal is observed that is proportional to the bound fraction of probe.

In certain embodiments, the peptide probe used in the HTS is TR-IP20. In one embodiment, the concentration of TR-IP20 is less than about 50 nM. In another embodiment, the concentration of TR-IP20 is from about 30 nM-50 nM. In another embodiment, the concentration of TR-IP20 is about 30 nM, 35 nM, 40 nM, 45 nM or 50 nM. In another embodiment, the concentration of TR-IP20 is about 40 nM.

In one embodiment, the cyclic nucleotide used in the HTS method is cGMP.

In one embodiment, the concentration of TR-IP20 is less than about 50 nM, the concentration of the C-subunit is less than about 75 nM and the concentration of R-subunit is in about 1 to about 3 molar excess of the C-subunit. In some embodiments, the concentration of TR-IP20 is from about 30 nM-50 nM, the concentration of the C-subunit is about 50 nM-75 nM, and the concentration of R-subunit is in about 1 to about 3 molar excess of the C-subunit. In one embodiment, the following concentrations are used for screening: 40 nM of TR-IP20, 64 nM of C-subunit and 77 nM of R-subunit.

To assess the quality of the HTS assay, the Z-factor, a statistical parameter that considers both dynamic range and data variation, can be calculated [Zhang, J. H., et al., (1999), A Simple Statistical Parameter for Use in Evaluation and Validation of High Throughput Screening Assays. *J Biomol Screen* 4, 67-73]. A 384-well format in 50 µL can be used for screening and Z-factors can be calculated separately for agonists and antagonists. Agonists increase the FP response, from the starting half maximal response, due to weakening the R-C complex. Consequently, an agonistic Z-factor is calculated between the half maximal binding response (for example, by activation with 3 µM of cGMP), and full probe binding response (induced with, for example, a saturating cGMP concentration of 500 µM). Alternately, antagonists lower the FP response by preventing cGMP from binding. An antagonistic Z-factor is calculated between half maximal probe binding and no probe binding (by competition with 50 µM of the antogonist, Rp-8-Br-cAMPS). Example 4 further describes calculation of the Z-factor.

Resistance to ATP Competitors

Current protein kinase high throughput screens identify small molecule effectors through their ability to modulate enzyme catalysis. In general, as the affinity of ATP for protein kinases is low (e.g. the affinity of ATP for the PKA C-subunit is around 25 µM), these screens are more likely to identify ATP competitive inhibitors. Binding of a peptide substrate (kemptide, LRRASLG, SEQ ID 2) does not influence ATP binding to PKA C-subunit [Lew, J., et al., (1997), Synergistic binding of nucleotides and inhibitors to cAMP-dependent protein kinase examined by acrylodan fluorescence spectroscopy, *J Biol Chem* 272, 1507-1513]. However, ATP affinity is improved by IP20 as seen from FIG. 3, the IP20 binding is sensitive to ATP. Thus, in certain embodiments, the FP based HTS assay provided herein is more resistant to compounds that compete with ATP, especially since an ATP concentration of 2 mM is used in the screen. For example, the potent ATP competitors, H89 (Ki of 49 nM) and staurosporine (Ki of 49 nM of 7 nM), tested in the HTS format at 200 µM showed no reduction in FP signal due to competition of these compounds with ATP.

Further provided are compounds capable of modulating the activity of protein kinase A identified by the screening method provided herein.

In some embodiments, provided herein are methods of using such identified compounds for the treatment, prevention and amelioration of various PKA-mediated diseases. Diseases that respond to PKA targeted small molecule drugs include but are not limited to solid tumors (e.g. breast cancer) and T cell response to HIV infection that are responsive to inhibitors of cAMP activation. Activators mimicking cAMP activation are used in the treatment, prevention or amelioration of systemic lupus erythematosus (SLE) autoimmune disease and lymphoma. Examples of cancers include cancers of brain (gliomas), breast, colon, head and neck, kidney, lung, liver, melanoma, ovarian, pancreatic, prostate, sarcoma, or thyroid.

D. Formulation of Pharmaceutical Compositions

The pharmaceutical compositions provided herein contain therapeutically effective amounts of one or more of compounds provided herein that are useful in the prevention, treatment, or amelioration of RAF kinase, including BRAF kinase, mediated diseases or one or more of the symptoms thereof.

The compositions contain one or more compounds provided herein. The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art.

In the compositions, effective concentrations of one or more compounds or pharmaceutically acceptable salt, solvate, hydrate or prodrug is (are) mixed with a suitable pharmaceutical carrier or vehicle. The concentrations of the compounds in the compositions are effective for delivery of an amount, upon administration, that treats, prevents, or ameliorates one or more of the symptoms of RAF kinase, including BRAF kinase, mediated diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of RAF kinase mediated diseases.

Typically a therapeutically effective dosage should produce a serum concentration of active ingredient of from about 1 ng/ml to about 50-100 µg/ml. The pharmaceutical compositions typically should provide a dosage of from about 10 mg to about 4000 mg of compound per kilogram of body weight per day. Pharmaceutical dosage unit forms are prepared to provide from about 10 mg to about 1000 mg and in certain embodiments, from about 10 mg to about 500 mg, from about 20 mg to about 250 mg or from about 25 mg to about 100 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing RAF kinase, including BRAF kinase, mediated diseases. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including, but not limited to, orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. In one embodiment, the effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001%-100% active ingredient, in certain embodiments, about 0.1-85%, typically about 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as RAF kinase, including BRAF kinase mediated diseases. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, *lycopodium* and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. In one embodiment, the composition is administered as an aqueous solution with hydroxypropyl-beta-cyclodextrin (HPBCD) as an excipient. In one embodiment, the aqueous solution contains about 1% to about 50% HPBCD. In one embodiment, the aqueous solution contains about 1%, 3%, 5%, 10% or about 20% HPBCD.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose, hydroxypropyl-beta-cyclodextrin (HPBCD) or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, 100-500 mg, 10-500 mg, 50-250 mg or 25-100 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used. In another embodiment, polymeric materials can be used. In yet another embodiment, a controlled release system can be placed in proximity of the therapeutic target, i.e., thus requiring only a fraction of the systemic dose. In some embodiments, a controlled release device is introduced into a subject in proximity of the site of inappropriate immune activation or a tumor. The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

7. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture containing packaging material, a compound or pharmaceutically acceptable derivative thereof provided herein, which is effective for treatment, prevention or amelioration of one or more symptoms of diseases or disorders associated with PKA activity, within the packaging material, and a label that indicates that the compound or composition, or pharmaceutically acceptable derivative thereof, is used for the treatment, prevention or amelioration of one or more symptoms of diseases or disorders associated with PKA activity.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder associated with PKA activity.

E. Methods of Using the Compounds and Compositions

Methods of treating, preventing, or ameliorating one or more diseases associated with PKA activity using the compounds and compositions provided herein are provided. In practicing the methods, effective amounts of the compounds or compositions containing therapeutically effective concentrations of the compounds are administered. In certain embodiments, the methods provided herein are for the preventing, or ameliorating cancer or and diseases of the immune system.

In one embodiment, a therapeutically effective dosage to treat the disease should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared, e.g., to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

In certain embodiments, the methods provided herein are for the preventing, or ameliorating one or more symptoms of cancers. Examples of cancers include, but are not limited to, lung cancer, head and neck squamous cancers, colorectal cancer, prostate cancer, breast cancer, acute lymphocytic leukemia, adult acute myeloid leukemia, adult non Hodgkin's lymphoma, brain tumors, cervical cancers, childhood cancers, childhood sarcoma, chronic lymphocytic leukemia, chronic myeloid leukemia, esophageal cancer, hairy cell leukemia, kidney cancer, liver cancer, multiple myeloma, neuroblastoma, oral cancer, pancreatic cancer, primary central nervous system lymphoma, and skin cancer.

The following examples are provided for illustrative purposes only and are not intended to limit the scope of the claimed subject matter.

EXAMPLES

General Methods

The inhibitor peptide IP20 (sequence Thr-Thr-Tyr-Ala-Asp-Phe-Ile-Ala-Ser-Gly-Arg-Thr-Gly-Arg-Arg-Asn-Ala-Ile-His-Asp) was synthesized at the University of California at San Diego (UCSD) in the Peptide and Oligonucleotide Core Facility and purified by HPLC. Succinimidyl esters of (5,6)-carboxyfluorescein (5,6-FAM) and Texas red-X were from Invitrogen (Carlsbad, Calif.). Rp-8-Br-cAMPS was from Axoora (San Diego, Calif.). Cyclic nucleotides (Adenosine 3',5'-cyclic monophosphate (cAMP), 2'-Deoxyadenosine 3':5'-cyclic monophosphate (dexoy-cAMP) and Guanosine 3',5'-cyclic monophosphate (cGMP)) and PKI (14-24) amide (sequence Gly-Arg-Thr-Gly-Arg-Arg-Asn-Ala-Ile-His-Asp-NH$_2$) were from Aldrich (Milwaukee, Wis.). ATP competitive inhibitors (H89 and staurosporine) were from LC Laboratories (San Diego, Calif.).

Protein Expression and Purification

The most stable constructs for the C- and R-subunits were used to minimize reagent preparation for HTS. These were the C199A mutant of the C-subunit and the Δ1-91 deletion mutant of the type Iα R-subunit, lacking the dimerization docking domain and thus unable to dimerize. Compared to wildtype the C199A mutant exhibits an identical binding profile with Flu-IP20 while the binding and activation characteristics of the Δ1-91 deletion mutant is almost the same as wildtype RIα [Herberg, F. W., et al. (1994), Crosstalk between domains in the regulatory subunit of cAMP-dependent protein kinase: influence of amino terminus on cAMP binding and holoenzyme formation, *Biochemistry* 33, 7485-7494]. The C199A mutant of recombinant murine catalytic subunit were expressed and purified from *E. coli* using methods known in the art, for example, see Gangal, M., et al., (1998), Backbone flexibility of five sites on the catalytic subunit of cAMP-dependent protein kinase in the open and closed conformations, *Biochemistry* 37, 13728-13735 and Su, Y., et al. (1995), Regulatory subunit of protein kinase A: structure of deletion mutant with cAMP binding domains. *Science* 269, 807-813.

Fluorescence Polarization Readings

Fluorescence readings were taken on a GeniosPro microplate reader (Tecan, Research triangle park, NC) with solid black 96-well untreated Costar (Corning, cat no. 3915) or 384-well medium binding Fluotrac-200 plates (Greiner, cat no. 781076). Fluorescein FP readings were with 485 nm excitation (20 nm bandpass) and 535 nm emission (20 nm bandpass) filters using the supplied 510 nm dichroic mirror. Texas red FP readings were with 570 nm excitation (20 nm bandpass) and 630 nm emission (30 nm bandpass) filters using a 590 nm dichroic mirror from Tecan.

FP values are reported in arbitary units of millipolarization (mP), and calculated with, $$mP = 1000 \cdot \frac{I_\| - G \times I_\perp}{I_\| + G \times I_\perp},$$

where $I_\|$ and $I_\perp$ are the intensity emissions in the parallel ($I_\|$) and perpendicular ($I_\perp$) directions, after background correction, relative to the plane of excitation and G-factors for fluorescein and texas red were calculated with green low polarization (P3089) and red low polarization (P2889) standards from Invitrogen.

All Dose dependent binding experiments were performed at 12 different concentrations using a two-fold dilutions series and in at least duplicate.

Example 1

Synthesis of Labeled IP20

IP20 was derivatized at the N-terminus with Fluorescein (Flu-IP20) or Texas red-X (TR-IP20) through amino conjugation with succinimidyl activated dye.

To synthesize Flu-IP20, 1 mg of (5,6)-FAM succinimidyl ester and 2 mg of IP20 in PBS containing 50% DMF were incubated overnight at 4° C. with gentle agitation. The fluorescent peptide was purified by C18 reverse phase HPLC with a water-acetonitrile gradient (0.08% TFA). Flu-IP20 eluted in 38% acetonitrile.

To synthesize TR-IP20, 1 mg of Texas red-X succinimidyl ester and 2 mg of IP20 in PBS containing 80% DMF were incubated overnight at 4° C. with gentle agitation. The fluorescent peptide was purified by C18 reverse phase HPLC and eluted in 49% acetonitrile.

Example 2

Binding Experiments

Flu-IP20 and TR-IP20 dose responses were measured by adding 5 μL of C-subunit to 45 μL of buffer containing Flu-IP20 or TR-IP20. Final concentrations were: C-subunit (512 nM to 0.5 nM), 1 nM or 50 nM Flu-IP20, 50 mM HEPES (pH 7.0), 0.005% Triton-X100, 10 mM $MgCl_2$, 2 mM ATP and 2 mM DTT.

Figure 3:
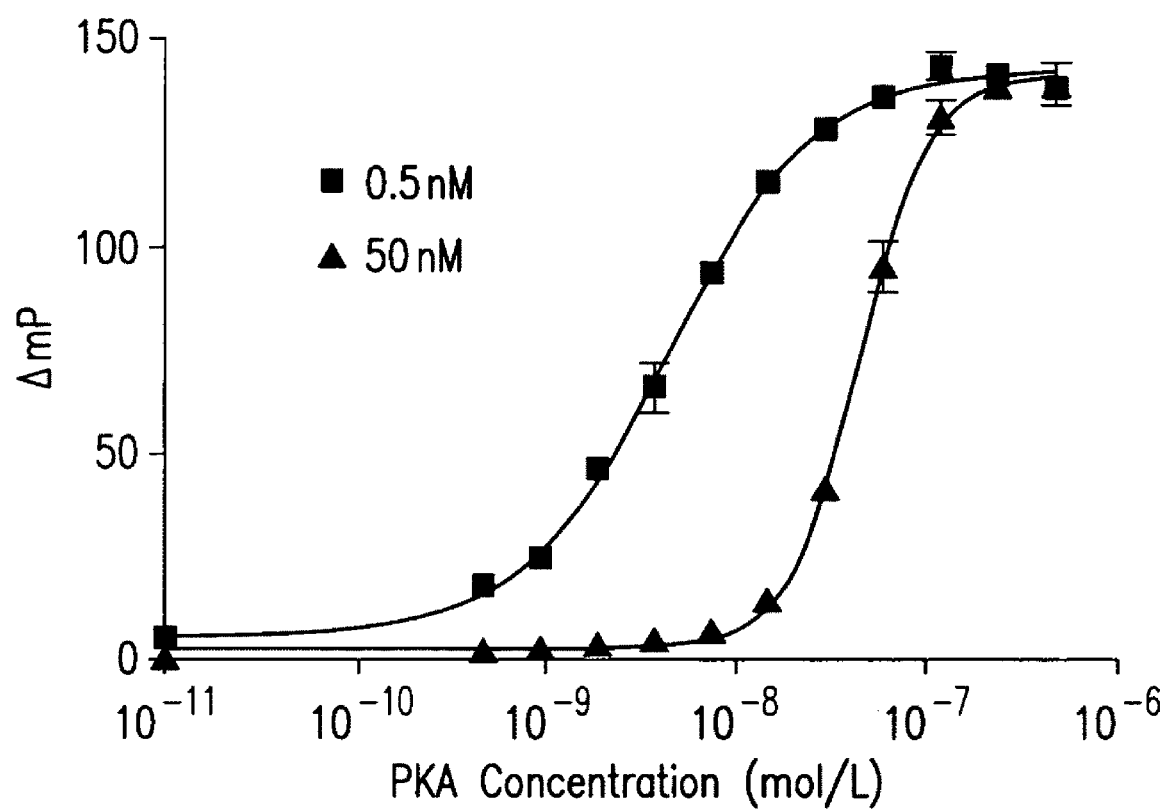
FIG. 3 shows dissociation constant of Flu-IP20 at 0.5 nM and 50 nM.

The concentration used for Flu-IP20 (1 nM) was below the reported Kd for IP20 (2.3 nM) and the subsequent apparent Kd for Flu-IP20 in this experiment (4.4 nM) demonstrates that N-terminal labeling does not impair binding. At higher Flu-IP20 concentrations the hill slope for this response increases (FIG. 3). The steeper dose dependence can be attributed to a titration effect where the concentration of Flu-IP20 is higher than the Kd for this binding event and not due to a complex binding mechanism such as protein or peptide aggregation.

ATP Dependence of IP20 Binding:

Measuring the ATP dose response was performed by adding 55 μL of ATP to 110 μL of buffer containing Flu-IP20 and C-subunit. Final concentrations were: ATP (12.8 μM to 12.5 nM), 2 nM Flu-IP20, 7 nM C-subunit, 50 mM HEPES (pH 7.0), 0.005% Triton-X100, 10 mM $MgCl_2$, and 2 mM DTT.

Figure 4:
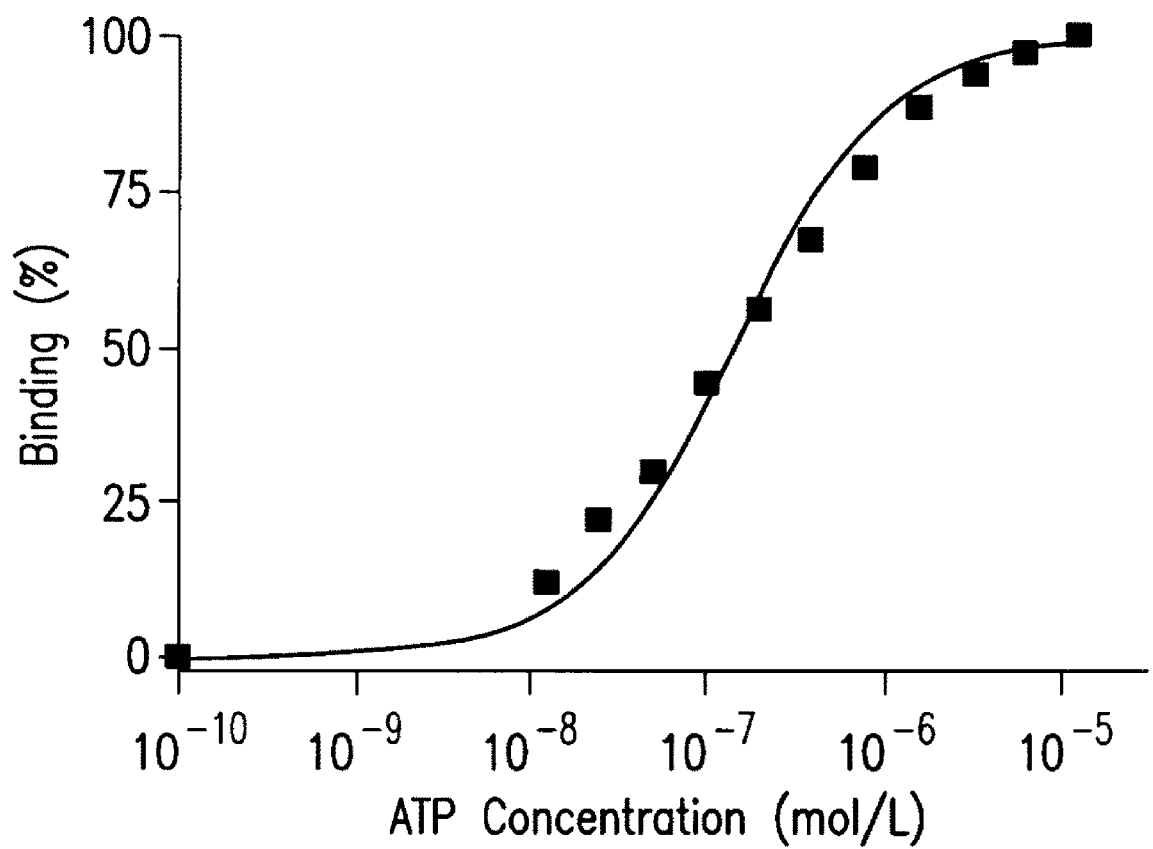
FIG. 4 demonstrates sensitivity of Flu-IP20 and C-subunit binding to ATP.

The affinity of the C-subunit for R-subunit or IP20 is dependent on ATP. This effect is synergistic since in the presence of the R-subunit or IP20 the affinity of the C-subunit for ATP is enhanced by over 2000-fold [Lew, J., et al., (1997). Synergistic binding of nucleotides and inhibitors to cAMP-dependent protein kinase examined by acrylodan fluorescence spectroscopy, *J Biol Chem* 272, 1507-1513]. This finding was corroborated by showing that the interaction between Flu-IP20 and C-subunit is sensitive to ATP concentration (FIG. 4). As a consequence all FP studies were performed at saturating amounts of ATP (2 mM) and $MgCl_2$ (10 mM).

Competition with PKI (14-24):

Competition experiments with PKI (14-24) were performed by adding 5 μL of peptide to 45 μL of buffer containing Flu-IP20 and C-subunit. Final concentrations were: PKI (14-24) (100 μM to 0.156 μM), 1 nM Flu-IP20, 5 nM C-subunit, 50 mM HEPES (pH 7.0), 0.005% Triton-X100, 10 mM $MgCl_2$, 2 mM ATP and 2 mM DTT.

This study proved that the interaction between C-subunit and fluorescently labeled IP20 was specific, the truncated version of IP20, PKI (14-24), competes with Flu-IP20 for binding to C-subunit. Flu-IP20 is displaced in a dose dependent manner by PKI (14-24) with an $IC_{50}$ of 2.7 μM (FIG. 5).

Example 3

Activation Studies

Type IαPKA holoenzyme was formed in-situ by combination of C-subunit and 1.2 molar excess of R-subunit with saturating amounts of ATP and $MgCl_2$. The concentration dependence for cyclic nucleotides was performed by adding 1 μL of cyclic nucleotide in DMSO to 49 μL buffer containing TR-IP20, C- and R-subunits. Final concentrations were: cAMP (20 μM to 20 nM) or cGMP (204 μM to 200 nM) or cTzMP (102 μM to 100 nM) or deoxy-cAMP (2 mM to 2 μM), 40 nM TR-IP20, 64 nM C-subunit, 77 nM R-subunit, 50 mM HEPES (pH 7.0), 0.005% Triton-X100, 10 mM MgCl$_2$, 2 mM ATP and 2 mM DTT.

Example 4

High-Throughput Assay Format

The high throughput screening (HTS) was performed by addition of 1 µL of a test compound in DMSO to 49 µL buffer containing TR-IP20, C-subunit, R-subunit, and cGMP. Final concentrations were: test compound (25 µM), 40 nM TR-IP20, 64 nM C-subunit, 77 nM R-subunit, 3 µM cGMP, 50 mM HEPES (pH 7.0), 0.005% Triton-X100, 10 mM MgCl$_2$, 2 mM ATP and 2 mM DTT.

The Z' factor was calculated with, $$Z' = 1 - \frac{3(\sigma_{pos} = \sigma_{neg})}{|\mu_{pos} - \mu_{neg}|},$$

with the mean (µ) and standard deviation (σ) of the positive and negative control responses.

An agonistic Z'-factor was calculated between the half maximal and maximal FP response, while the antagonistic Z'-factor was calculated between the minimal and half maximal FP response. The maximal FP response was calculated by adding 1 µL cGMP in DMSO (500 µM final) to 49 µL HTS mix. Half maximal binding was calculated when 1 µL DMSO was used instead and minimal FP response was calculated by adding 1 µL Rp-8-Br-cAMPS in DMSO (50 µM final). Final DMSO concentration was 2%.

Antagonism by Rp-8-Br-cAMPS was measured with the HTS format. Final concentrations were: Rp-8-Br-cAMPS (41 µM to 40 nM), 40 nM TR-IP20, 64 nM C-subunit, 77 nM R-subunit, 3 µM cGMP, 50 mM HEPES (pH 7.0), 0.005% Triton-X100, 10 mM MgCl$_2$, 2 mM ATP and 2 mM DTT.

Figure 8:
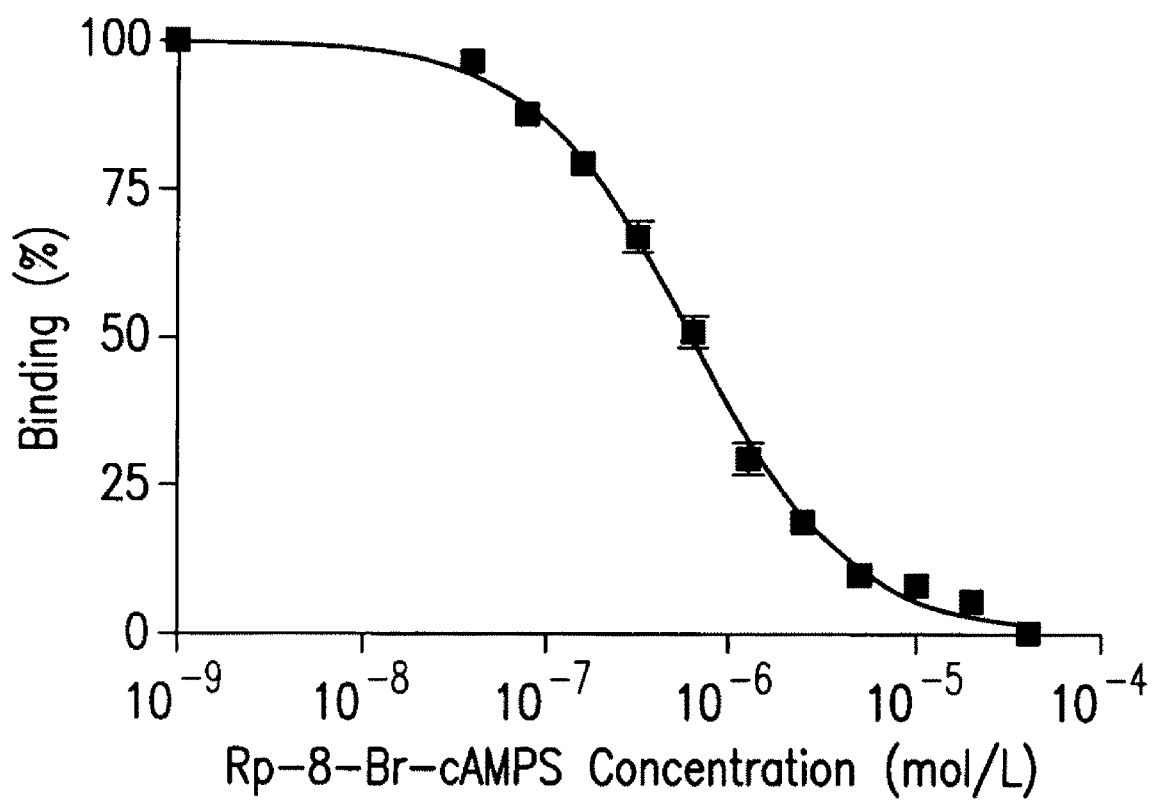
FIG. 8 shows antagonism by Rp-8-Br-cAMPS.
Figure 9:
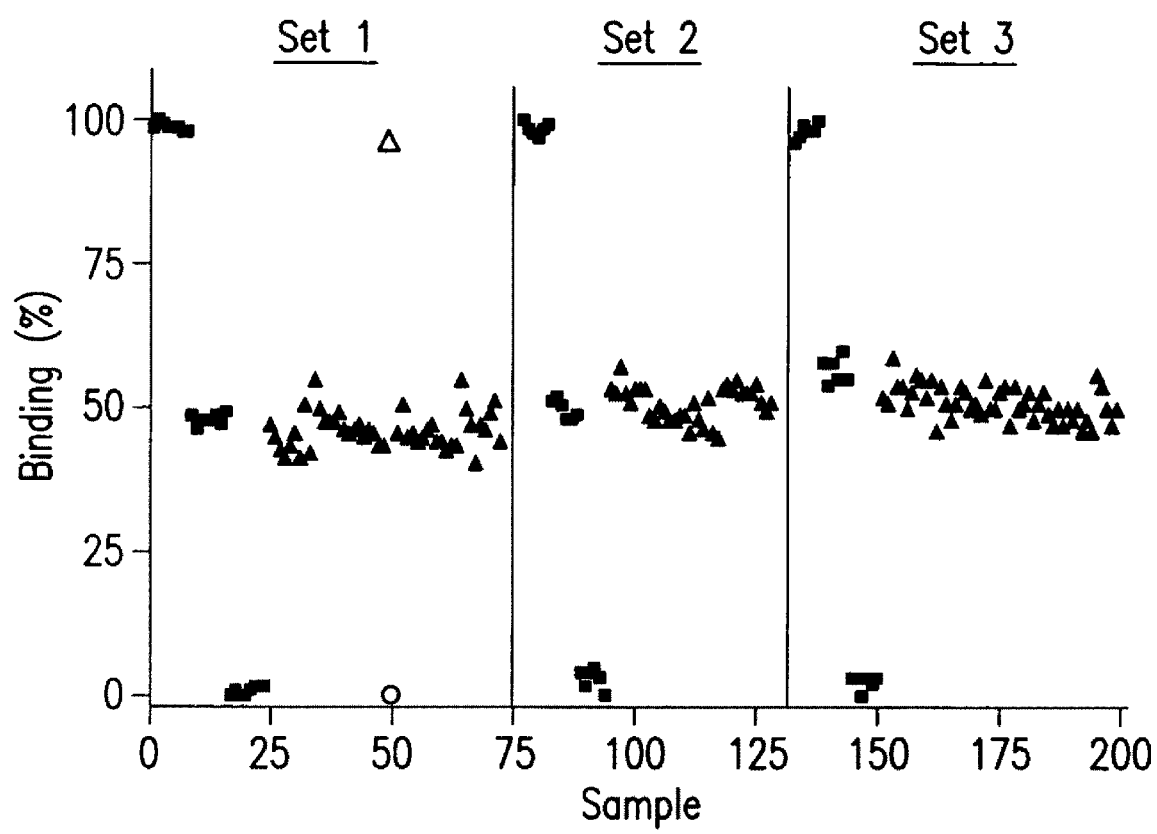
FIG. 9 shows high throughput screen with three sets of compounds tested at 25 µM.
Figure 10:
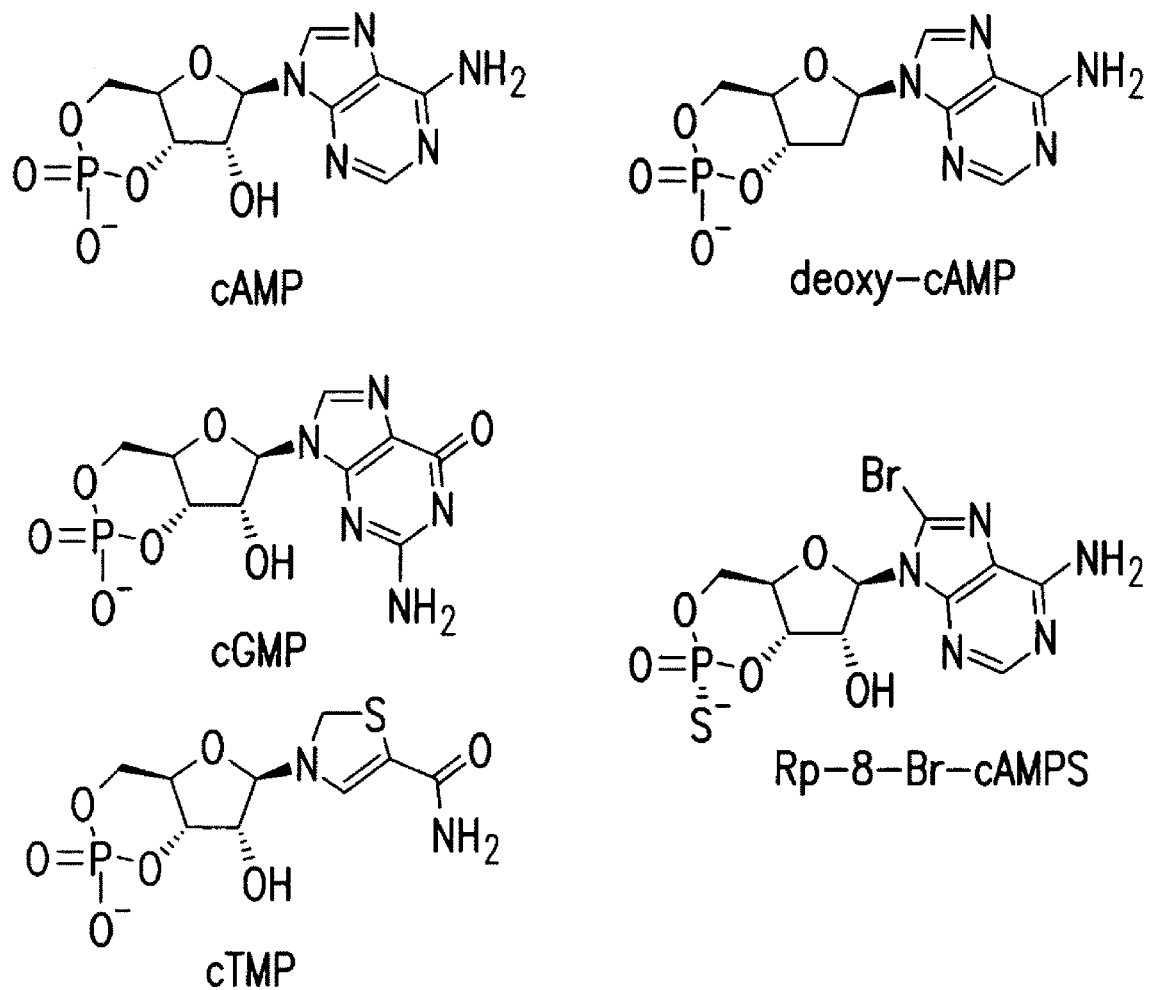
FIG. 10 provides structures of exemplary cyclic nucleotide used herein.
Figure 11:
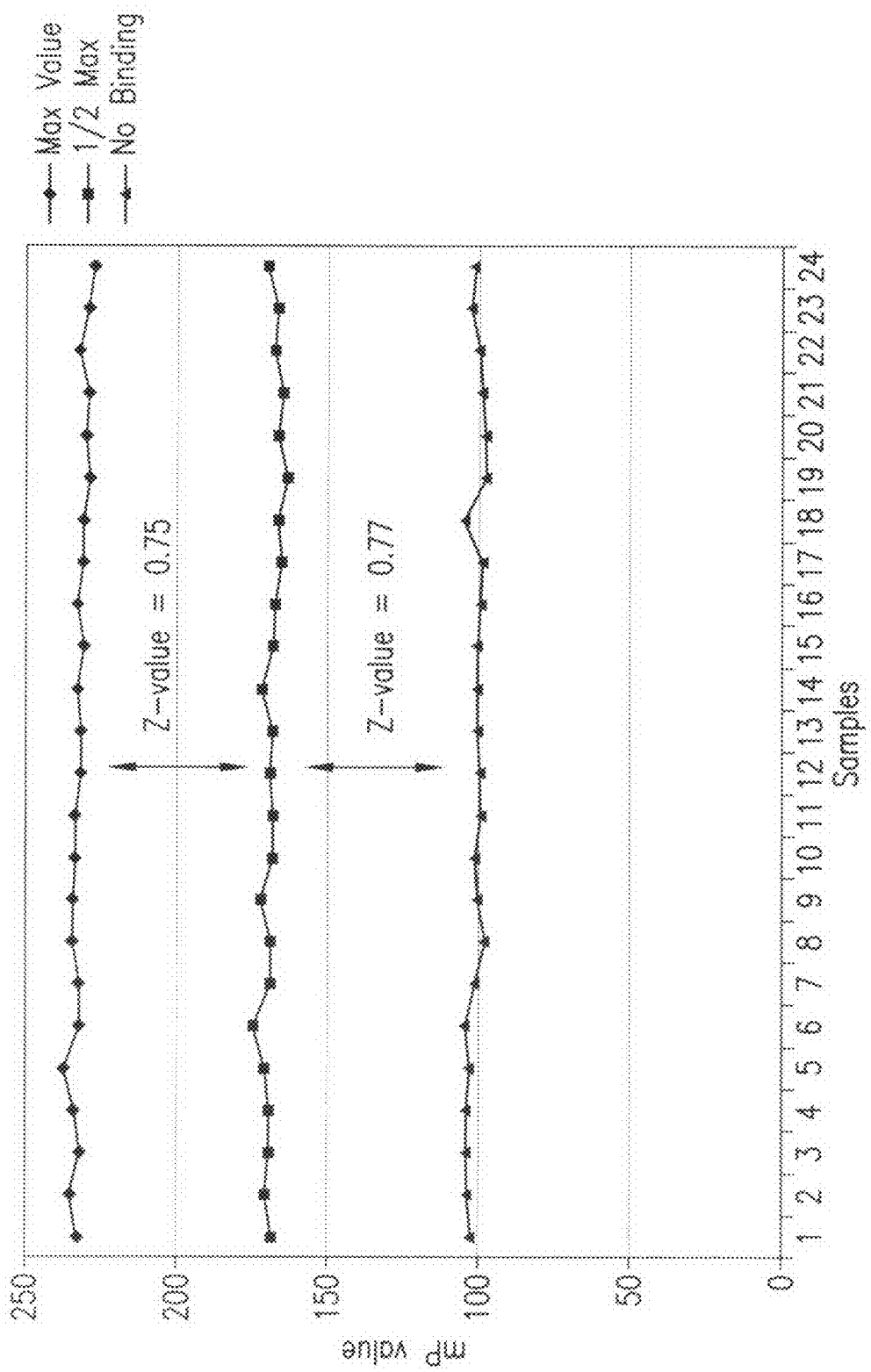
FIG. 11 provides Z values for HTS assay.

The dose response for Rp-8-Br-cAMPS as a competitor of cGMP could be accurately measured, even in HTS mode (FIG. 8). To assess the quality of the HTS assay, the Z-factor that considers both dynamic range and data variation, was calculated [Zhang, J. H., Chung, T. D., and Oldenburg, K. R. (1999). A Simple Statistical Parameter for Use in Evaluation and Validation of High Throughput Screening Assays. *J Biomol Screen* 4, 67-73.]. A 384-well format in 50 µL was used for screening and Z-factors were calculated separately for agonists and antagonists. Agonists increased the FP response, from the starting half maximal response, due to weakening the R-C complex. Consequently, an agonistic Z-factor was calculated between the half maximal binding response (by activation with 3 µM of cGMP), and full probe binding response (induced with a saturating cGMP concentration of 500 µM). Alternately, antagonists lowered the FP response by preventing cGMP from binding. An antagonistic Z-factor was calculated between half maximal probe binding and no probe binding (by competition with 50 µM of the antagonist, Rp-8-Br-cAMPS). A measure of the precision of an HTS assay is the Z-value. Typically values above 0.4 or 0.5 are acceptable. As shown in FIG. 11, a Z-value of >0.7 was observed for this assay.

Finally, to validate the assay, screening was performed on a selection of nucleotide and xanthine derivatives. FIG. 8 shows three sets, totaling 134 compounds, tested at 25 µM. A compound is recognized as an agonist if the FP reading is significantly higher than with 3 µM of cGMP alone. Alternately, a compound is recognized as an antagonist if the FP reading is significantly lower than with 3 µM of cGMP alone. Included in Set 1 are the known PKA effectors 8-Cl-cAMP (agonist) and Rp-8-Br-cAMPS (antagonist). No other compounds in these screens showed a significant effect.

Since modifications will be apparent to those of skill in the art, it is intended that the claimed subject matter be limited only by the scope of the appended claims.

---

What is claimed is:

1. A method for screening compounds that modulate an activity of protein kinase A comprising:
   i) contacting a test compound with a mixture comprising a fluorescently-labeled peptide probe, a cyclic nucleotide or an analog thereof, a C-subunit of protein kinase A and an R-subunit of protein kinase A; and
   ii) comparing the fluorescent polarization of the mixture before and after contacting with the test compound;
   wherein said fluorescently-labeled peptide probe binds at said C-subunit.

2. The method of claim 1, wherein the method is performed in a multi-well format.

3. The method of claim 1, wherein the compound is an agonist of protein kinase A.

4. The method of claim 1, wherein the compound is an antagonist of protein kinase A.

5. The method of claim 1, wherein said fluorescently-labeled peptide probe is selected from heat stable protein kinase inhibitors.

6. The method claim 1, wherein said fluorescently-labeled peptide probe binds to the C-subunit with nanomolar affinity.

7. The method of claim 1, wherein said fluorescently-labeled peptide probe comprises a peptide sequence with SEQ ID 1.

8. The method of claim 1, wherein said fluorescently-labeled peptide probe is a peptide sequence with SEQ ID 1.

9. The method of claim 8, wherein said fluorescently-labeled peptide probe comprises an N-terminus labeled with carboxyfluorescein.

10. The method of claim 9, wherein the concentration of said fluorescently-labeled peptide probe is below about 4.4 nM.

11. The method of claim 9, wherein the concentration of said fluorescently-labeled peptide probe is about 1 nM.

12. The method of claim 8, wherein said fluorescently-labeled peptide probe comprises an N-terminus labeled with a far-red dye.

13. The method of claim 12, wherein the N-terminus of said fluorescently-labeled peptide probe is labeled with Texas red-X.

14. The method of claim 1, wherein the C-subunit comprises a wildtype or C199A mutant of the C-subunit.

15. The method of claim 1, wherein the R-subunit comprises a Δ1-91 deletion mutant.

16. The method of claim 1, wherein the mixture comprises less than about 75 nM C-subunit.

17. The method of claim 1, wherein the mixture comprises about 50 nM-75 nM C-subunit.

18. The method of claim 1, wherein the mixture comprises about 64 nM C-subunit.

19. The method of claim 1, wherein the mixture comprises the R-subunit in a concentration of about 1 to about 3 molar excess of C-subunit.

20. The method of claim 1, wherein the mixture comprises about 77 nM R-subunit.

21. The method of claim 1, wherein the cyclic nucleotide is cAMP or cGMP.

22. The method of claim 1 adapted for high-throughput screening.

23. The method of claim 22, wherein the mixture comprises less than about 50 nM TR-IP-20, less than about 75 nM C-subunit and about 1 to about 3 molar excess of the R-subunit over the C-subunit.

24. The method of claim 22, wherein the mixture comprises about 40 nM of TR-IP20, about 64 nM C-subunit and about 77 nM R-subunit.

25. The method of claim 22, wherein the cyclic nucleotide is cGMP.

* * * * *